(12) United States Patent
Chenoll Cuadros et al.

(10) Patent No.: US 11,202,813 B2
(45) Date of Patent: Dec. 21, 2021

(54) LACTOBACILLUS RHAMNOSUS BACTERIUM FOR TREATMENT OF E.G. BACTERIAL VAGINOSIS

(71) Applicant: Ferring B.V., Hoofddorp (NL)

(72) Inventors: Maria Empar Chenoll Cuadros, La Pobla de Vallbona (ES); Beatriz Casinos Ramo, Chiva (ES); Angela Silva Angulo, Paterna (ES); Daniel Ramon Vidal, La Eliana (ES); Salvador Genoves Martinez, Aldaia (ES)

(73) Assignee: FERRING B.V., Hoofddorp (NL)

( * ) Notice: Subject to any disclaimer, the term of this patent is extended or adjusted under 35 U.S.C. 154(b) by 0 days.

(21) Appl. No.: 16/808,242

(22) Filed: Mar. 3, 2020

(65) Prior Publication Data

US 2020/0268815 A1 Aug. 27, 2020

Related U.S. Application Data

(62) Division of application No. 15/740,807, filed as application No. PCT/EP2016/065074 on Jun. 29, 2016, now Pat. No. 10,588,926.

(30) Foreign Application Priority Data

Jun. 29, 2015 (EP) .................................... 15174222

(51) Int. Cl.
| | |
|---|---|
| A61K 9/48 | (2006.01) |
| A61K 35/747 | (2015.01) |
| A61K 9/00 | (2006.01) |
| A23L 33/135 | (2016.01) |
| A61K 9/02 | (2006.01) |
| A61K 9/19 | (2006.01) |
| A61K 47/36 | (2006.01) |
| A61P 15/02 | (2006.01) |
| A61P 31/04 | (2006.01) |

(52) U.S. Cl.
CPC .......... *A61K 35/747* (2013.01); *A23L 33/135* (2016.08); *A61K 9/0034* (2013.01); *A61K 9/0095* (2013.01); *A61K 9/02* (2013.01); *A61K 9/19* (2013.01); *A61K 9/48* (2013.01); *A61K 47/36* (2013.01); *A61P 15/02* (2018.01); *A61P 31/04* (2018.01)

(58) Field of Classification Search
None
See application file for complete search history.

(56) References Cited

U.S. PATENT DOCUMENTS 10,588,926 B2  3/2020  Chenoll Cuadros et al.

FOREIGN PATENT DOCUMENTS

| EP | 0 257 007 | 2/1988 |
| WO | WO-2012/035028 | 3/2012 |

OTHER PUBLICATIONS

Chenolli, "Complete Genome Sequence of *Lactobacillus rhamnosus* strain BPL5 (CECT 8800), a Probiotic for Treatment of Bacterial Vaginosis," Genome Announc. 4(2):e00292-16. (2016).
Kiss et al., "Vaginal Lactobacillus microbiota of healthy women in the late first trimester of pregnancy," BJOG, 114:1402-1407(2007).
Notice of Allowance dated Nov. 6, 2019, in U.S. Appl. No. 15/740,807 (U.S. Pat. No. 10,588,926).
Office Action dated Jul. 23, 2019, in U.S. Appl. No. 15/740,807 (U.S. Pat. No. 10,588,926).
Office Action dated Mar. 5, 2019, in U.S. Appl. No. 15/740,807 (U.S. Pat. No. 10,588,926).
Pithva et al. "Probiotic Attributes of Autochthonous *Lactobacillus rhamnosus* strains of Human Origin," Appl. Biochem. Biotechnol. 173: 259-277 (2014).
Reid et al. "Selection of *Lactobacillus* Strains for Urogenital Probiotic Applications", J Infect. Dis. 183 (Suppl.): S77-S80 (2001).
Reid et al., "Oral use of Lactobacillus rhamnosus GR-1 and L. fermentum RC-14 significantly alters vagina flora: randomized, placebo-controlled trial in 64 healthy women," FEMS Immunology and Medical Microbiology 35, 131-134 (2003).
Related PCT appln. No. PCT/EP2016/ 055074 (published as WO 2017/001440 A1), International Search Report and written Opinion, dated Oct. 17, 2016.
Related PCT appln. No. PCT/EP2016/055074 (published as WO 2017/001440 A1), International Preliminary Report on Patentability (IPRP), dated Jan. 2, 2018.
Siaterlis et al., "Effect of culture medium and cryoprotectants on the growth and survival of probiotic lactobacilli during freeze drying," Letters in Applied Microbiology, 48(2009) 295-301.
Office Action dated May 7, 2020, in Japanese Application No. 2017-567804.
Pastaud, C., "Interet Des Probiotiques Dans Le Traitement De La Vaginose Bacterienne," These Pour Le Diplome D'Etat De Docteur En Pharmacie, Universite De Limoges Faculte De Pharmacie (Dec. 13, 2013) 93 pages.
Zhong et al., "Lactobacillus rhamnosus GR-1 and Lactobacillus reuteri RC-14 for Treatment and Prevention of Vaginal Infections," J Int. Obstet Gynecol, vol. 40, No. 5, pp. 428-431 (Oct. 2013).

*Primary Examiner* — Jennifer E Graser
(74) *Attorney, Agent, or Firm* — Foley & Lardner LLP

(57) ABSTRACT

A novel lactic acid *Lactobacillus rhamnosus* bacterium suitable for treatment of e.g. bacterial vaginosis.

2 Claims, No Drawings

LACTOBACILLUS RHAMNOSUS BACTERIUM FOR TREATMENT OF E.G. BACTERIAL VAGINOSIS

CROSS-REFERENCE TO RELATED APPLICATIONS

The present application is a divisional of U.S. application Ser. No. 15/740,807, filed Dec. 29, 2017, which is the U.S. National Stage of International Application PCT/EP2016/065074, filed Jun. 29, 2016, which claims priority to European Patent Application No. 15174222.8, filed Jun. 29, 2015.

FIELD OF THE INVENTION

The present invention relates to a novel lactic acid *Lactobacillus rhamnosus* bacterium suitable for treatment of e.g. bacterial vaginosis.

BACKGROUND ART

Bacterial vaginosis (BV) is one of the most common disorders in women of reproductive age. According to the US Centers for Disease Control and Prevention (CDC), risk factors for BV include douching and having new or multiple sex partners. BV is caused by an imbalance of naturally occurring bacterial microbiota and can be microbiologically characterized by replacement of the lactobacilli-predominant vaginal microbiota by potential pathogenic vaginal bacteria. The change from a healthy, $H_2O_2$ and lactic acid producing lactobacilli-dominated microbiota to a complex multispecies microbiota can occur relatively quickly and result in BV.

As discussed in e.g. EP0257007 (filed 1987)—it has been known for long time that Bacterial vaginosis (BV) is accompanied by a rise in pH (rise from normal/healthy pH of approximately 4 to a pH above 4.5) and a microbial dysbiosis in which the usually dominant *Lactobacillus* vaginal microbiota is overwhelmed by an overgrowth of predominantly anaerobic organisms.

EP2509610B1 (HSO Health Care, Vienna—filed 13 Sep. 2011 and published/granted in 2013) provides a summary of herein relevant background prior art.

As discussed in EP2509610B1—the healthy human vagina is dominated by a variety of *Lactobacillus* species, which play an essential role in protecting women from urogenital infection. Lactobacilli have the ability to adhere to vaginal epithelia, to inhibit the adhesion and growth of pathogens, deplete nutrients otherwise available to pathogens, and modulate the host immune response and microenvironment. Most importantly, Lactobacilli metabolize the glycogen contained in the cells of the vaginal vault, forming lactic acid as the final product. Thus, in a healthy vagina, pH-values of around 4.0 are reached, a level at which many pathogens cannot flourish.

When administrated to a woman in the form of a pharmaceutical composition (e.g. vaginal capsules for vaginal administration)—the protective effect of Lactobacilli against potential pathogens in the vagina is generated through the metabolic activity of the Lactobacilli. The bacteria consume glycogen and other sources of glucose and produce lactic acid. The low pH generated in this manner is harmful to the less desirable bacteria and fungi and thus protects the vaginal mucosa against infections.

Because vaginal infection is an important mechanism of disease responsible for preterm birth, maintaining the natural, healthy balance of the *Lactobacillus* microbiota in the vagina is particularly important during pregnancy. A deficiency in Lactobacilli can upset the microbial balance in the vagina, frequently resulting in the syndrome of bacterial vaginosis, which may be associated with a quantitative and qualitative shift from normally occurring Lactobacilli to a mixed microbiota dominated by anaerobic bacteria. According to the art, bacterial vaginosis may be characterized by a complete loss of Lactobacilli and a concomitant increase in Gram-variable and Gram-negative rods, primary among them *Gardnerella vaginalis* as well as *Bacteroides, Prevotella*, and *Mobiluncus* species. However, loss of vaginal Lactobacilli also leaves nonpregnant women susceptible to infection which may result in endometritis or even pelvic inflammatory disease.

During menopause, involution of the female genital tract occurs, reflecting possibly a built-in biologic life expectancy interrelated with the neurohypophyseal endocrine axis. The major universal change is vaginal atrophy. Vaginal dryness, burning, itching and dyspareunia are frequent complaints along with dysuria, urinary frequency and recurrent infections. The genitourinary atrophy following menopause is associated with a decline in estrogen secretion accompanied by depletion of Lactobacilli and increased colonization by pathogenic microorganisms associated with bacterial vaginosis and urinary tract infections. In post-menopausal women, vaginal estriol therapy reduces *Escherichia coli* colonization and increases the numbers of Lactobacilli, with the result that the incidence of recurrent urinary and genital tract infections drops significantly.

Several species of *Lactobacillus* have been described to populate the vagina to varying degrees. For some time the microbiota of healthy women of childbearing age was believed to be dominated by *L. acidophilus* and *L. fermentum*, followed by *L. brevis, L. jensenii* and *L. casei*. In another study on the vaginal *Lactobacillus* microbiota the authors found that the vaginal microbiota of most participants was dominated by a single *Lactobacillus* species, with the presence of other species showing wide individual variability. The most frequently occurring species were *L. crispatus, L. gasseri, L. iners*, and *L. jensenii*. In another study, the most commonly isolated *Lactobacillus* strains were *L. jensenii, L. acidophilus, L. casei*, and *L. gasseri*. In recent Austrian studies, the predominant *Lactobacillus* species identified by species-specific PCR, namely *L. crispatus, L. gasseri, L. jensenii*, and *L. rhamnosus* were used to generate DNA fingerprints. *L. crispatus, L. gasseri, L. jensenii* and *L. rhamnosus* can be regarded as the predominant species in the vagina.

To remedy deficiencies in the *Lactobacillus* microbiota (and hence, in the protective capability of the vaginal microbiota), the administration of vaginal suppositories containing Lactobacilli is the most common way of Lactobacilli substitution. Some authors believe that the topical use of Lactobacilli is a safe and promising treatment for the prevention of vaginosis and recurrent urinary tract infections.

While vaginal supplementation is a long-standing, widely accepted practice for Lactobacilli substitution, oral administration of a *Lactobacillus* preparation represents a new concept for the restitution of a normal vaginal microbiota. Relatively recent results indicate that the probiotic strains *L. rhamnosus* GR-1 (ATCC 55826) and *L. reuteri* RC-14 (ATCC 55845) can be taken orally on a daily basis for two months without any side effects. The consumption then resulted in a significant improvement of the vaginal microbiota in terms of increased Lactobacilli presence and decreased yeast and coliforms. While one group of authors discussed the beneficial effects in terms of an alteration in mucosal immunity or of probiotic bacteria ascending to the vagina from the rectal area, another group recently demonstrated, by species-specific PCR-amplification, that *L. rhamnosus* GR-1 and *L. reuteri* RC-14 can be delivered to the vaginal environment when administered orally.

In view of above discussed prior art—the invention as described in EP2509610B1 relates to a use of a combination of specific deposited strains of *L. crispatus, L. rhamnosus, L. jensenii* and/or *L. gasseri* for treatment of bacterial vaginosis (BV). In table 11 on page 15 is shown that e.g. deposited *L. rhamnosus* (DSM22560) has a relatively good capability to lower pH.

SUMMARY OF THE INVENTION

The problem to be solved by the present invention is to provide a novel *Lactobacillus rhamnosus* strain with good properties in particular in relation to the treatment of vaginal and female genital and urogenital infection and/or urinary tract infections caused by *Lactobacillus* deficiency (such as e.g. bacterial vaginosis).

As can be seen in working examples below the herein described novel *L. rhamnosus* strain with the registration number CECT 8800 (herein also termed BPL005) has a number of good/improved in particular in relation to the treatment of e.g. bacterial vaginosis.

The results of working Example 1 herein demonstrated following relevant positive characteristics of the isolated CECT 8800 (=BPL005) *L. rhamnosus* strain:

1: It was isolated de novo from isolates from vagina of healthy women—i.e. there is prima facie no reason to believe it is not a novel strain as such;

2: Random Amplified Polymorphic DNA (RAPD) profile demonstrated that the strain is different to the others and 16S rRNA sequencing showed that BPL005 is a unique *L. rhamnosus* strain;

3: BPL005 had the highest capacity of the vagina isolated strains to reduce pH levels;

4: In assays without pH control BPL005 gave a rapid pH decreasing effect. The rapid production of lactic acid in the case of BPL005 strain is in agreement with its high capacity to reduce pH in a short time. Regarding the production of the rest of acids, strain BPL005 was the best producer of the tested strains;

5: With respect to resistance to gynaecological commercial products—strain BPL005 was resistant to the highest concentration tested and no inhibitions were observed;

6: Genome sequencing of the whole genome of strain BPL005 showed that it had a unique contig of 3.023 Mb—i.e. the genome sequence was not a prior art described sequence.

As discussed above—it has been known for long time that Bacterial vaginosis (BV) is accompanied by a rise in pH (rise from normal/healthy pH of approximately 4 to a pH above 4.5) and a microbial dysbiosis in which the usually dominant *Lactobacillus* vaginal microbiota is overwhelmed by an overgrowth of predominantly anaerobic organisms.

Accordingly, the fact that herein described novel CECT 8800 (=BPL005) *L. rhamnosus* strain has a very good capacity to reduce pH levels is important in relation to use of the strain the treatment of e.g. bacterial vaginosis.

In short and without being limited to theory—based of the herein described good properties of the herein described novel CECT 8800 (=BPL005) *L. rhamnosus* strain, there is no reason to believe that it would not be useful for the treatment of vaginal and female genital and urogenital infection and/or urinary tract infections caused by *Lactobacillus* deficiency (such as e.g. bacterial vaginosis).

The results of working Example 2 herein showed that strain BPL005 had similar pH-reducing levels than the best probiotics tested of herein relevant commercial gynaecological probiotic products.

The results of working Example 3 herein showed good efficiency of strain BPL005 in the production process at lab-scale (volume 1 L) and data of the made lyophilized powder showed that the BPL005 strain has obtained a good stability in a 15 months period.

The results of working Example 4 herein showed good efficiency of strain BPL005 in the production process at industrial-scale (volume 1500 L) and data of the made lyophilized powder showed that the BPL005 strain has obtained a very good stability.

In order to be able to make a herein relevant commercial product it is evident that it is an advantage that the *Lactobacillus* strain can be produced properly at industrial scale—accordingly, working Example 4 herein demonstrates further advantageous properties of herein described novel CECT 8800 (=BPL005) *L. rhamnosus* strain.

Accordingly, a first aspect of the invention relates to a lactic acid *L. rhamnosus* bacterium with the registration number CECT 8800 (herein also termed BPL005) or a mutant thereof, wherein the mutant strain is obtained by using the deposited strain as starting material, and wherein the mutant has retained or further improved the capacity to reduce pH levels of CECT 8800.

A second aspect of the invention relates to a dietetic or a pharmaceutical composition comprising the bacterium of the first aspect and/or any herein described embodiment thereof.

The term "dietetic" relates according to the art to diet or the regulation of food or feed intake. Accordingly a dietetic composition is a composition that is suitable for being added to a food product for a human or a feed product for an animal.

A third aspect of the invention relates to a dietetic or pharmaceutical composition according to the second aspect and/or any herein described embodiment thereof, for use in the treatment of a disorder in a woman, wherein the disorder is imbalance of naturally occurring vaginal bacterial microbiota, vaginal infection, female genital infection, urogenital infection or urinary tract infection.

A fourth aspect of the invention relates to a dairy product, a drink product, a food product for human nutrition and/or a feed product for animal nutrition characterized in that the product contains a dietetic composition according to the second aspect and/or any herein described embodiment thereof.

Embodiment of the present invention is described below, by way of examples only.

DETAILED DESCRIPTION OF THE INVENTION

Novel *Lactobacillus rhamnosus* Strain

A sample of the novel *Lactobacillus rhamnosus* strain BPL005 has been deposited at CECT (Colección Española de Cultivos Tipo) under the accession number CECT 8800 with a deposit date of 15 Dec. 2014. The deposit has been made under the conditions of the Budapest Treaty on the International Recognition of the Deposit of Microorganisms for the Purposes of Patent Procedure.

The first aspect of the invention relates to the herein described novel strain or "a mutant thereof".

It is clear for the skilled person that by using the deposited strain as starting material, the skilled reader can by conventional mutagenesis or re-isolation techniques routinely obtain further mutants or derivatives thereof that retain the herein described relevant features and advantages. Accordingly, the term "a mutant thereof" of the first aspect relates to mutant strains obtained by using the deposited strain as starting material.

Alternatively expressed—the invention relates to a method for obtaining a mutant strain of lactic acid *L. rhamnosus* bacterium with the registration number CECT 8800 comprising the following steps:

(i): making mutants of the lactic acid *L. rhamnosus* bacterium with the registration number CECT 8800;

(ii): analyzing the in step (i) made mutants and identify a mutant strain that has retained or further improved the capacity of CECT 8800 to reduce pH levels; and (iii): isolating the in step (ii) identified mutant strain to thereby obtain the mutant strain of lactic acid *L. rhamnosus* bacterium with the registration number CECT 8800, wherein the mutant strain has retained or further improved the capacity of CECT 8800 to reduce pH levels.

Preferably, the first aspect relates to a lactic acid *L. rhamnosus* bacterium with the registration number CECT 8800 (herein also termed BPL005).

The article (Chenoll E, Codoñer F M, Martinez-Blanch J F, Ramón D, Genovés S, Menabrito M. 2016. Complete genome sequence of *Lactobacillus rhamnosus* strain BPL5 (CECT 8800), a probiotic for treatment of bacterial vaginosis. Genome Announc 4(2):e00292-16. doi:10.1128/genomeA.00292-16. Copyright© 2016 Chenoll et al.) was published in April, 2016—i.e. after the 29 Jun. 2015 EP15174222.8 priority date of the present application. This article discloses the complete genome sequence of the lactic acid *L. rhamnosus* bacterium with the registration number CECT 8800 of the present invention. It is evident that it was routine work for the skilled person to obtain a mutant strain of CECT 8800 even without the knowledge of the genome sequence—with the sequence this is even easier.

A Dietetic or a Pharmaceutical Composition—Second Aspect of the Invention

As discussed above—a second aspect of the invention relates to a dietetic or a pharmaceutical composition comprising the bacterium of the first aspect and/or any herein described embodiment thereof.

The dietetic composition generally comprises dietetic or nutritional acceptable adjuvants and/or excipients.

The pharmaceutical composition generally comprises pharmaceutical acceptable adjuvants and/or excipients.

Typically, such composition comprises the bacteria in a concentrated form including frozen, dried or freeze-dried concentrates typically having a concentration of viable cells, which is in the range of $10^4$ to $10^{14}$ cfu (colony forming units) per gram of the composition. It may be preferred that the range is in the range of $10^6$ to $10^{14}$ cfu (colony forming units) per gram of the composition or is in the range of $10^8$ to $10^{14}$ cfu (colony forming units) per gram of the composition. A relevant range may also be in the range of $10^6$ to $10^{13}$ cfu (colony forming units) per gram of the composition.

It may be preferred that the composition comprises freeze-dried (alternatively expressed lyophilized) bacteria.

The composition may as further components contain cryoprotectants (e.g. maltodextrine) and/or conventional additives including nutrients such as yeast extracts, sugars and vitamins.

If the composition comprises freeze-dried bacteria then is preferably comprises suitable cryoprotectants (e.g. maltodextrine).

As understood by the skilled person in the present context—the dietetic or a pharmaceutical composition as described herein will in certain embodiments comprise a multiplicity of strains either belonging to the same species or belonging to different species. A typical example of such a useful combination of lactic acid bacteria in a composition as described herein is a mixture of a *Leuconostoc* sp. and one or more *Lactococcus* subsp. such as *Lc. lactis* subsp. *lactis*, *Lc. lactis* subsp. *cremoris* or *Lc.s lactis* subsp. *lactis* biovar. *diacetylactis*.

It may also be e.g. *L. crispatus*, *L. rhamnosus*, *Lactobacillus jensenii* and/or *L. gasseri*.

Application forms of the compositions according to the inventions suitable for oral intake or topical vaginal administration may be preferred. As an example, probiotic bacteria for female use can be administered orally in the form of capsules, or (filled in sachets) suspended in a drink, or in the form of fermented milk (yogurt). When administered orally, they are expected to survive passage through the stomach and duodenum (displaying a certain stability towards acid and bile) and temporarily colonize the gut. From there, small numbers of bacteria will ascend to the vagina and (again temporarily) colonize the vaginal mucosa. Probiotic bacteria can also be used conventionally as vaginal capsules or suppositories and directly applied to the vagina. The protective effect of Lactobacilli against potential pathogens in the vagina is generated through the metabolic activity of the Lactobacilli. The bacteria consume glycogen and other sources of glucose and produce lactic acid. The low pH generated in this manner is harmful to the less desirable bacteria and fungi and thus protects the vaginal mucosa against infections. Therefore, a composition according to the invention may be administered in the form of suppositories, vaginal capsules for vaginal administration or as coated capsules, tablets, sachets, pills, pearls, vials for oral intake as well as yogurt, yogurt drinks, fermented milk, juices, and other fermented drinks and foods.

Use for Treatment of Disorder in a Woman—Third Aspect of the Invention

As discussed above—a third aspect of the invention relates to a dietetic or pharmaceutical composition according to the second aspect and/or any herein described embodiment thereof, for use in the treatment of a disorder in a woman, wherein the disorder is imbalance of naturally occurring vaginal bacterial microbiota, vaginal infection, female genital infection, urogenital infection or urinary tract infection.

As understood by the skilled person in the present context—in relation to the disorder in a women e.g. a dietetic or pharmaceutical composition as described herein will many times be used in order to restore and/or maintain a healthy vaginal bacterial microbiota.

The third aspect may alternatively be formulated as relating to a method for treatment of a disorder in a woman, wherein the disorder imbalance of naturally occurring vaginal bacterial microbiota, vaginal infection, female genital infection, urogenital infection or urinary tract infection, in a human woman comprising administering a relevant amount of a dietetic or pharmaceutical composition according to the second aspect and/or any herein described embodiment thereof to the human woman.

Examples of a herein relevant disorder is vaginosis, vaginitis, chronic bacterial vaginosis, chronic yeast infection, chronic urinary tract infection in menopause, atrophic vaginitis, vaginosis or bacterial vaginosis.

In a preferred embodiment, the disorder in a woman is bacterial vaginosis (BV).

In addition, the compositions according to the invention are particularly suitable for use in the treatment or prevention of asymptomatic and recurrent bacterial vaginosis in pregnancy or preterm delivery caused by bacterial vaginosis.

Dairy Product, a Drink Product, a Food Product Etc—Fourth Aspect of the Invention As discussed above—a fourth aspect of the invention relates to a dairy product, a drink product, a food product for human nutrition and/or a feed product for animal nutrition characterized in that the product contains a dietetic composition according to the second aspect and/or any herein described embodiment thereof.

Dairy products of the present invention can consist of milk, yogurt, cheese, homogenized products (based on milk, cheese, fruit), fermented or non-fermented milk (including powdered milk, nonlactose containing milk, milk shakes) containing probiotics. Therapeutic cheese can be obtained by the addition of suitable probiotic microorganisms in a concentrated dried form in a certain processing phase of the cheese in order to guarantee the supply of the dose of the microorganisms necessary for the organism. The drinks can be instantaneous drinks or water containing the compositions according to the present invention.

Said integrators, dairy and food products are suitable for use in the treatment the same disorders in a woman as discussed above—i.e. for use in the treatment of a disorder in a woman, wherein the disorder is imbalance of naturally occurring vaginal bacterial microbiota, vaginal infection, female genital infection, urogenital infection or urinary tract infection.

An embodiment of the invention relates to a method of manufacturing a fermented food or fermented feed product comprising adding a lactic acid *Lactobacillus rhamnosus* bacterium of first aspect to a food or feed product starting material and keeping the thus inoculated starting material under conditions where the lactic acid bacterium is metabolically active.

Useful food product starting materials include any material which is conventionally subjected to a lactic acid bacterial fermentation step such as milk, vegetable materials, meat products, fruit juices, must, doughs, soya and batters.

The fermented products, which are obtained by the method, include as typical examples dairy products such as fermented milk, yogurt, cheese including fresh cheese products or mozzarella, and buttermilk.

In further embodiments, the substrate material is a starting material for an animal feed such as silage, e. g. grass, cereal material, peas, alfalfa or sugar-beet leaf, where bacterial cultures are inoculated in the feed crop to be ensiled in order to obtain a preservation hereof, or in protein rich animal waste products such as slaughtering offal and fish offal, also with the aims of preserving this offal for animal feeding purposes.

EXAMPLES

Example 1: Isolation and Characterization of *L. rhamnosus* BPL005 of the Invention Material and Methods 1. Isolation and Selection of the Strains In order to obtain isolates from vagina of healthy women, samples were taken from middle area of the vagina of fourteen healthy premenopausal women aged between 18 and 45. The exclusion criteria were stated pregnant or lactating women, menstruating at the time of sampling, or with an antimicrobial therapy against previous vaginitis.

Swabs were spread in MRS agar plates and incubated anaerobically at 37° C. Gram-positive, non-sporulated rods were selected as presumptive lactobacilli. Pure cultures were long-term stored (−20° C.) in glycerol for further analysis.

2. Molecular Identification

In order to ensure that isolates are unique, agarose Random Amplified Polymorphic DNA (RAPD) profiles were generated and duplicate isolates were rejected.

Molecular identification was carried out by 16S rRNA gene sequencing as Chenoll et al. (Novel Probiotic *Bifidobacterium bifidum* CECT 7366 strain active against the pathogenic bacterium *Helicobacter pylori*. 2011. Applied and Environmental Microbiology. 77(4): 1335-1343). Briefly, DNA from pure cultures was extracted and purified and 16S rDNA was amplified by PCR technology. Amplification products were purified and sequenced. Identification was achieved by comparing sequences obtained with the BLAST database (http://blast.ncbi.nlm.nih.gov/Blast.cgi).

3. Selection of the Best pH-Reducing Strain

In order to study the capacity of lactobacilli strains to reduce pH levels, standardized cultures of the strains were grown in de Man, Rogosa and Sharpe (MRS) medium during 17 h at 37° C. Final pH was measured with the aid of a pH meter. Assays were performed in triplicate. Once experiments performed separately, the combination of the most reducing strains to decrease pH levels was tested. To perform this assay, both strains were co-cultivated in MRS medium during 17 h at 37° C., and final pH was measured with the aid of a pH meter.

4. Identification of the Organic Acid Profile

To obtain the organic acid profile of selected strains, each strain was cultured anaerobically at 37° C. in 1 L fermentors (Biobundle; Applikon), in the industrial medium optimized in Biopolis for lactobacilli. For each strain, two conditions were assayed: with and without pH control. In both cases, levels of pH were monitored during the assay. Samples were collected throughout the assay. For organic acids quantification, 0.8 mL of cell-free supernatant was mixed by vortexing with 0.2 mL of a mixture containing 5% meta-phosphoric acid, copper sulfate (1.56 mg/mL) and 50 mM 4-methyl valeric acid as an internal standard. Samples were then filtered by 0.45 µm pore size and diluted ½ and ⅒.

The evaluation of organic acids was performed by HPLC chromatography. An aliquot of 10 µL of processed samples was injected onto a HPLC Alliance 2695 (Waters) equipped with a Rezex column (ROA Organic Acid (H+) 8% 300×7.8 mm, 8 um [Premium]) under conditions defined by manufacturer. Detection was achieved by an index of refraction detector (2414 Waters). The eluent was degassed $H_2SO_4$ 2.5 mM at an isocratic flow rate of 0.6 mL/min. In all cases, quantification curves were constructed adding the mixed previously defined.

5. Resistance to Commercial Products.

In order to test the resistance of strain BPL005 to different gynaecological products, aliquots of direct stocks of each product were dissolved in broth medium to 5120 μg/ml, and 0.22 μm filtered. Stock solutions were stored at −80° C. From the first dilution, ½ serial dilutions were performed in a range of 512-0.125 μg/ml. Inoculums were obtained directly from a 24 h colony, resuspended in saline solution to 0.5 MacFarland and diluted 1/20 in saline solution. Assays were performed in multiwell plates and incubated anaerobically at 37° C. during 24 h. The Minimum Inhibitory Concentration (MIC) was established as the minimum concentration in which the antibiotic exerts a clear inhibition (with no growth). In the case of products with high turbidity, assays included a second step in which 5 μL of 24 h broth of BPL005 in the IST medium in the presence of serially diluted commercial products were dropped in agar plates to confirm the growth of the probiotic.

6. Genome Sequence

To obtain the whole genome sequence and analysis of the complete genome of strain BPL005, genome sequencing and bioinformatic analysis are being performed.

i) Sequencing:

To obtain the whole genome of the selected strain, a high concentrated pellet was obtained from the master cell bank and high pure DNA was manually extracted following Pitcher et al. (Rapid extraction of bacterial genomic DNA with guanidium thiocyanate. 1989. Letters in Applied Microbiology. 8 (4): 151-156). Sequencing has been performed with the aid of Pacific Biosciences platform (PacBio).

ii) Bioinformatic Analyses:

Raw sequences obtained from the whole genome sequencing have been assembled constructing a scaffolding to be used for genome annotation. tRNAs, rRNA s and open Reading Frames (ORFs) will be predicted. ORFs functionality will be annotated by comparing each ORF against a database containing all sequences from the bacteria kingdom. Once gene functionality associated to each ORF, virulence and antibiotic resistance genes will be searched and listed.

Results

1. Isolation and Selection of the Strains

In total, fourteen samples were obtained and spread in MRS agar plates in order to obtain isolates. Fourteen strains were obtained out of 100 isolates recovered. All of them were obtained from vagina samples. Once recovered, strains were long-term stored (−20° C.) in glycerol for further analysis. The isolates obtained were classified on the basis of Gram staining and cell morphology. Fourteen Gram-positive, non-sporulated rods were classified as presumptive lactobacilli and thus selected for further identification.

2. Molecular Identification

Once the isolates recovered, agarose RAPD profiles were performed in order to reject duplicate isolates. On the basis of RAPD profiles, the fourteen isolates were grouped in six different strains. Strains were identified by 16S rRNA sequencing (Table 1) and *Lactobacillus* strains were selected for further studies (Table 2). In addition, collection strains *L. crispatus* CECT 4840 and *L. iners* DSM 13335 were included in the study.

TABLE 1

Groups obtained by RAPD profile and 16S rRNA sequencing.

| Genus | Isolates (strains) |
|---|---|
| *Lactobacillus* | 14 (6) |
| Pathogens | 10 (5) |
| "Uncultured bacterium" | 6 (6) |
| Others | 14 (14) |

TABLE 2

*Lactobacilli* strains obtained.

| Identification | Strain |
|---|---|
| *Lactobacillus casei* | BPL013 |
| *L. jensenii* | BPL016 |
|  | BPL017 |
|  | BPL035 |
|  | BPL044 |
| *L. rhamnosus* | BPL005 |

3. Selection of the Best pH-Reducing Strain

The capacity of strains to reduce pH levels was studied. Table 3 summarizes the results obtained. In assays performed with only one strain, pH levels decreased in all cases. The highest pH reduction was obtained in the case of strain *L. rhamnosus* BPL005, being the final pH 3.82.

TABLE 3 pH levels obtained in growth cultures of *lactobacilli* strains (assay with pure cultures).

| Strain | pH |
|---|---|
| Control (medium without culture) | 6.1 |
| *L. crispatus* CECT4840 | 4.55 |
| *L. iners* DSM13335 | 4.52 |
| *L. casei* BPL013 | 4.30 |
| *L. jensenii* BPL016 | 4.46 |
| *L. jensenii* BPL017 | 4.30 |
| *L. jensenii* BPL035 | 4.34 |
| *L. jensenii* BPL044 | 4.61 |
| *L. rhamnosus* BPL005 | 3.82 |

On the basis of pH reduction results, strain *L. rhamnosus* BPL005 and *L. casei* BPL013 were selected for further studies.

4. Identification of the Organic Acid Profile

Organic acids have been described as inhibitory metabolites and also as compounds with a prebiotic effect. In this sense, strains BPL005 and BPL013 were analysed on the basis of their production of organic acids in 1 L fermentations. Regarding pH decreasing in assays without pH control—in the case of strain BPL005, pH started decreasing very fast. At 5 hours of fermentation, pH level was 3.7 and at 10 hours of fermentation pH reached its minimum (pH 3.0). In the case of BPL013 strain, pH decreased gradually, with the lowest pH at 30 hours of fermentation.

Tables 4-5 show the production of organic acids. In the case of fermentations with pH control, samples were recovered at the end of the fermentation. In all cases, highest levels were obtained for lactic acid, being the highest concentrations 22.53 g/L in the case of BPL013 and 19.90 g/L for BPL005 strain, in fermentations with controlled pH. The rapid production of lactic acid in the case of BPL005 strain is in agreement with its high capacity to reduce pH in a short time. The production of lactic acid was followed by a decrease in pH in both strains, being more remarkable in the case of strain BPL005.

Regarding the production of the rest of acids, strain BPL005 was the best producer in all cases. It has been reported that these organic acids could inhibit pathogen bacteria and yeasts (Juarez et al. Urogenital pathogen inhibition and compatibility between vaginal *Lactobacillus* strains to be considered as probiotic candidates. 2011. European Journal of Obstetrics & Gynecology and Reproductive Biology. 159: 399-406) In the case of lactic acid, levels obtained were higher than other previously described in above cited Juarez et al. reference.

TABLE 4

Levels of organic acids (g/L) obtained in BPL005 fermentations.

| | Organic acids concentration (g/L) | | | |
| --- | --- | --- | --- | --- |
| | no pH control | | | pH control |
| | 5 h | 22 h | 45 h | 22 h |
| Lactic acid | 3.172 ± 0.066 | 12.168 ± 0.223 | 15.635 ± 0.158 | 19.731 ± 0.232 |
| Acetic acid | 0.105 ± 0.050 | 0.123 ± 0.058 | 0.143 ± 0.058 | 0.145 ± 0.049 |
| Propionic acid | 0.740 ± 0.029 | 0.155 ± 0.029 | 0.210 ± 0.026 | 0.134 ± 0.013 |
| Butyric acid | 0.074 ± 0.041 | 0.074 ± 0.041 | 0.072 ± 0.039 | 0.082 ± 0.041 |
| Succinic acid | 0.114 ± 0.025 | 0.112 ± 0.042 | 0.157 ± 0.033 | 0.175 ± 0.008 |

TABLE 5

Levels of organic acids (g/L) obtained in BPL013 fermentations.

| | Organic acids concentration (g/L) | | | |
| --- | --- | --- | --- | --- |
| | no pH control | | | pH control |
| | 5 h | 30 h | 42 h | 42 h |
| Lactic acid | 0.479 ± 0.090 | 1.387 ± 0.096 | 10.093 ± 0.088 | 22.814 ± 0.397 |
| Acetic acid | 0.060 ± 0.051 | 0.065 ± 0.051 | 0.084 ± 0.054 | 0.109 ± 0.064 |
| Propionic acid | 0.058 ± 0.041 | 0.045 ± 0.030 | 0.058 ± 0.027 | 0.058 ± 0.023 |
| Butyric acid | ND | ND | ND | ND |
| Succinic acid | 0.092 ± 0.001 | 0.11 ± 0.002 | 0.104 ± 0.023 | 0.133 ± 0.032 |

ND: Not detected.

5. Resistance to Commercial Products Assays.

Results obtained with the gynaecological commercial products are summarized in Table 6. In all cases, strain BPL005 was resistant to the highest concentration tested and no inhibitions were observed, even at highest concentrations in products in gel and cream matrix.

TABLE 6

MIC values obtained for progesterone-based products.

| Product | MIC (mg/ml) |
| --- | --- |
| Ultrogestan | >20 mg/ml |
| Progeffik | >20 mg/ml |
| Prolutex | >20 mg/ml |
| Crinone | >22 mg/ml |
| Darstin | >2.22 mg/ml* |

*Higher concentration was not possible to test because of its initial concentration.

6. Genome Sequence

The whole genome of strain BPL005 has been sequenced. Whole genome extraction has been performed; identification of strain corroborated and sequencing has been applied. The assembly rendered a unique contig of 3.023 Mb. There were not sequences predicted as plasmids.

Conclusions

The results of this Example demonstrated following herein relevant positive characteristics of the isolated BPL005 *L. rhamnosus* strain:

1: It was isolated de novo from isolates from vagina of healthy women—i.e. there is prima facie no reason to believe it is not a novel strain as such;

2: Random Amplified Polymorphic DNA (RAPD) profile demonstrated that the strain is different to the others and 16S rRNA sequencing showed that BPL005 is a unique *L. rhamnosus* strain;

3: BPL005 had the highest capacity of the vagina isolated strains to reduce pH levels;

4: In assays without pH control BPL005 gave a rapid pH decreasing effect. The rapid production of lactic acid in the case of BPL005 strain is in agreement with its high capacity to reduce pH in a short time. Regarding the production of the rest of acids, strain BPL005 was the best producer of the tested strains;

5: With respect to resistance to gynaecological commercial products—strain BPL005 was resistant to the highest concentration tested and no inhibitions were observed;

6: Genome sequencing of the whole genome of strain BPL005 showed that it had a unique contig of 3.023 Mb—i.e. the genome sequence was not a prior art described sequence.

Example 2: Comparison of BPL005 with the Commercial Gynaecological Probiotics Material and Methods
Viable Cells in Product.

To study in depth the different commercial probiotic products now available in the market, a collection of 18 probiotics-based products was analysed. Products tested are summarized in Table 7. For each product, concentration was obtained by counts in MRS plates and functionality of strains was tested. To study the functionality, probiotic strains were isolated, identified by 16S rDNA sequencing and its capacity to decrease pH tested.

Ability to Reduce pH Levels

Probiotic strains were isolated from commercial products and stored at −80° C. Identification at species level was confirmed by 16S rDNA sequencing. For each strain, pH reduction assays were performed as explained above. BPL005 strain was included as a control.

Results
Viable Cells in Product

To study in depth the different commercial probiotic products now available in the market, a collection of 18 probiotics-based products was analysed. Products tested are summarized in Table 8. For each product, concentration was obtained by counts in MRS plates and functionality of strains was tested. To study the functionality, probiotic strains were isolated, identified by 16S rDNA sequencing and its capacity to decrease pH tested.

TABLE 8

Comparative analysis of commercial products.

| Commercial product | Kind of product | Viable bacteria (CFU/g) | Quantity (g) | Total viable bacteria (CFU) | Theoretical viable bacteria (CFU) |
|---|---|---|---|---|---|
| Ginegea *Candida* stick | Powder | 5.70E+09 | 2 | 1.14E+10 | 1.00E+09 |
| HydralinFlora | Capsules | 2.77E+10 | 0.20 | 5.53E+09 | 1.00E+08 |
| mediGYNE | Capsules | 1.30E+09 | 0.20 | 2.60E+08 | 1.00E+08 |
| GynOphilus LP[1] | Capsules | 1.78E+09 | 0.88 | 1.56E+09 | 877 mg[1] |
| GynOphilus[1] | Capsules | 4.00E+09 | 0.34 | 1.36E+09 | 341 mg[1] |
| FLORGYNAL TAMPON | Tampons | 1.18E+09 | 1.60 | 1.88E+09 | — |
| SYMBIO Vag | Hard vaginal capsule | 9.00E+08 | 2 | 1.80E+09 | 1.00E+09 |
| Muvagyn probiótico | Tampons | 2.20E+07 | 3.10 | 6.83E+07 | 1.00E+08 |
| Muvagyn Probiótico | Capsules | 1.80E+09 | 0.41 | 7.33E+08 | 1.00E+08 |
| Isadin α barcilus ISDIN | Soft vaginal capsule | 7.70E+08 | 2.82 | 2.17E+09 | 1.00E+08 |
| NORMOGIN 40 mg[1] | Capsules | 3.20E+06 | 1.00 | 3.20E+06 | 40 mg[1] |
| Lactonorm | Capsules | 6.40E+08 | 0.42 | 2.70E+08 | 1.00E+11[2] |
| ACIDIF CV | Capsules | 1.40E+08 | 1.05 | 1.47E+08 | 5.00E+08 |
| Vaginol[3] | Hard vaginal capsule | — | — | — | — |
| Gyno-canesflor | Capsules | 2.20E+10 | 0.34 | 7.41E+09 | 1.00E+08 |
| Floragyn[4] | Hard vaginal capsule | 5.90E+04 | 2.00 | 1.18E+05 | — |
| Lactoflorene Gyn | Hard vaginal capsule | 2.34E+05 | 0.62 | 1.44E+05 | 1.20E+06 |

[1]Dosis are given in mg, not in CFU;
[2]Viables in the time of encapsulation;
[3]No probiotics in the composition;
[4]Lysated probiotics

TABLE 7

Commercial products analysed.

| Commercial product | Kind of product |
|---|---|
| Ginegea *Candida* stick | Powder |
| HydralinFlora | Capsules |
| mediGYNE | Capsules |
| GynOphilus LP | Capsules |
| GynOphilus | Capsules |
| FLORGYNAL TAMPON | Tampons |
| Symbiovag | Capsules |
| SYMBIO Vag | Hard vaginal capsule |
| Muvagyn probiótico | Tampone |
| Muvagyn Probiótico | Capsules |
| Isadin α barcilus ISDIN | Soft vaginal capsule |
| NORMOGIN 40 mg | Capsules |
| Lactonorm | Capsules |
| ACIDIF CV | Capsules |
| Vaginol | Hard vaginal capsule |
| Gyno-canesflor | Capsules |
| Floragyn | Hard vaginal capsule |
| Lactoflorene Gyn | Hard vaginal capsule |

As shown in Table 8, results were very variable. Some of them showed viable cells lower than specifications.

Ability to Reduce pH Levels

Probiotic strains from commercial products were isolated and their ability to reduce pH levels tested. Table 9 shows the comparison obtained among them.

TABLE 9

Reduction of pH level obtained for commercial probiotics.

| Product | Probiotics isolated | Final pH |
|---|---|---|
| MediGYNE | *L. gasserii* | 4.33 |
| | *L. rhamnosus* | 3.55 |
| HydralinFlora | *L. plantarum* | 3.55 |
| GynOphilus LP | *L. casei rhamnosus* Döderlein | 4.20 |
| FLORGYNAL tampon | *L. rhamnosus* | 4.25 |
| | *L. fermentum* | 4.10 |
| Muvagyn | *L. gasserii* LN40 | 4.21 |
| | *L. fermentum* LN99 | 4.23 |
| | *L. rhamnosus* LN113 | 4.24 |
| Isadin α barcilus ISDIN | *L. plantarum* | 3.93 |
| GynOphilus | *L. casei rhamnosus* Döderlein | 4.17 |

TABLE 9-continued

Reduction of pH level obtained for commercial probiotics.

| Product | Probiotics isolated | Final pH |
|---|---|---|
| Lactonorm | L. acidophilus | 4.23 |
| BPL005 (control) | L. rhamnosus | 3.73 |

Results obtained showed strain BPL005 had similar pH-reducing levels than the best probiotics tested.

Conclusions

The results of this Example showed that strain BPL005 had similar pH-reducing levels than the best probiotics tested of herein relevant commercial gynaecological probiotic products.

Example 3: Evaluation of the Productivity of *Lactobacillus* Strain BPL005 in Laboratory-Scale Production (Volume 1 L)

Material and Methods

For the evaluation of productivity, a master cell bank and a working cell bank at −80° C. were constructed.

Laboratory-scale production was performed in 1 L fermentor (Biobundle; Applikon), in an industrial medium optimized for lactobacilli. Culture was obtained in standard conditions (Table 10), and cells were collected by centrifuging. After collected, pellet was resuspended in a maltodextrine-based carrier solution and frozen at −80° C. and lyophilized.

TABLE 10

Fermentation conditions

| Parameter | Value |
|---|---|
| OD Fermentator t 0 h | 0.1 |
| Temperature | 37° C. |
| Shaking | 100 rpm |
| Atmosphere | Anaerobiosis |
| pH | 6.3 |
| Culture medium | BRFS |

In order to evaluate the resistance of the strain to freezing and lyophilisation processes, cell viability was checked on MRS agar plates before being collected and after lyophilisation.

Study of Stability of Lyophilized Product

The lyophilized powder was vacuum-packaged and stored at 5° C. (±3° C.). Stability of the product was checked by counts in MRS during 15 months.

Results

In order to obtain the evaluation of strain BPL005 efficiency, a lab-scale production was performed. Results obtained are summarized in Table 11. Results obtained showed a good efficiency of strain BPL005 in the production process at lab-scale.

TABLE 11

Results obtained after 1 L fermentation.

| Parameter | Value |
|---|---|
| Time of harvest | 20 h |
| Final OD | 8.1 |

TABLE 11-continued

Results obtained after 1 L fermentation.

| Parameter | Value |
|---|---|
| Final CFU/ml in fermentor | $9 \times 10^9$ CFU/ml |
| Final CFU/g in lyophilized | $2.7 \times 10^{12}$ CFU/g |

The lyophilized powder was vacuum-packaged and stored at 5° C. Stability of the product was checked by counts in MRS. The BPL005 strain has obtained a good stability in a 15 months period.

Conclusions

The results of this Example showed good efficiency of strain BPL005 in the production process at lab-scale (volume 1 L) and data of the made lyophilized powder showed that the BPL005 strain has obtained a good stability in a 15 months period.

Example 4: Industrial Production of Lactobacilli BPL005 Strain (Volume 1500 L)

Material and Methods

Industrial Scale-Up Production

Industrial production was carried out in a 1500 L fermentor. Growth was performed in an industrial medium optimized for lactobacilli. Culture was obtained in standard conditions (anaerobically, controlling pH and temperature), and cells were collected by centrifuging in an industrial centrifuge.

Optimization of Lyophilisation

Once obtained, pellet was resuspended in carrier (maltodextrine-based) and lyophilised in an industrial lyophilizer. To obtain the capacity of the strain to resist lyophilisation process, viability was checked on MRS agar plates just after fermentation process and after industrial freeze-drying process. The purity of culture and lyophilised product was checked by electrophoretic RAPD (Random Amplification of Polymorphic DNA) profiles of randomly selected colonies.

Shelf-Life Evaluation of Bulk Powder.

Shelf-life of bulk powder is in study. Aliquots of bulk-powder are stored under 5° C. and 25° C. Evaluation will be performed periodically by counts on MRS agar.

Results

Industrial Scale-Up Production

Industrial production was carried out in a 1500 L fermentor following standard conditions. *Lactobacillus rhamnosus* BPL005 culture rendered $6.55 \times 10^9$ CFU/mL. This result is in agreement with results obtained in 1 L scale, and acceptable in terms of efficiency of the process.

Optimization of Lyophilisation

Counts obtained are summarized in Table 12. Results obtained showed a good efficiency of strain BPL005 to the production process at 1500 L scale.

TABLE 12

Results obtained after 1500 L fermentation.

| Time of harvest | 17 h |
|---|---|
| Final CFU/ml in fermentor | $6.55 \times 10^9$ CFU/ml |
| Final CFU/g in lyophilized | $5.53 \times 10^{11}$ CFU/g |

Shelf-Life Evaluation of Bulk Powder.

The stability obtained in the 1500 L production at 5° C. and 25° C. of the vacuum-packed lyophilized strain BPL005 showed that the product was very stable at a temperature of 5° C. Results obtained at 25° C. show an acceptable low decrease in numbers.

Conclusions

The results of this Example showed good efficiency of strain BPL005 in the production process at industrial-scale (volume 1500 L) and data of the made lyophilized powder showed that the BPL005 strain has obtained a very good stability.

The strain of *Lactobacillus rhamnosus* identified as strain BPL005 was deposited under the provisions of the Budapest Treaty at Colección Española de Cultivos Tipo (CECT) (Valencia, Spain) under accession number CECT 8800 on Dec. 15, 2014.

REFERENCES

1: EP0257007 (filed 1987)
2: EP2509610B1 (HSO Health Care, Vienna—filed 13 Sep. 2011 and published/granted in 2013)
3: Chenoll E, Codoñer F M, Martinez-Blanch J F, Ramón D, Genovés S, Menabrito M. 2016. Complete genome sequence of *Lactobacillus rhamnosus* strain BPL5 (CECT 8800), a probiotic for treatment of bacterial vaginosis. Genome Announc 4(2):e00292-16. doi:10.1128/genomeA.00292-16. Copy-right© 2016 Chenoll et al.—published in April, 2016

The invention claimed is:

1. A method for obtaining a mutant strain of lactic acid *Lactobacillus rhamnosus* strain BPL005 deposited at Colección Española de Cultivos Tipo (CECT) under accession number CECT 8800, comprising:

(i) obtaining strain BPL005;

(ii) making mutant strains from the strain BPL005 by a process selected from conventional mutagenesis and re-isolation techniques;

(iii) analyzing the mutant strains for capacity to reduce pH levels; and (iv) isolating a mutant strain that exhibits retained or further improved capacity to reduce pH levels relative to strain BLP005, when assessed by growing the strains in de Man, Rogosa and Sharpe (MRS) medium for 17 hours at 37° C. and thereafter measuring pH, to thereby obtain a mutant strain of lactic acid *Lactobacillus rhamnosus* strain BPL005, wherein the mutant strain has retained or further improved capacity to reduce pH levels relative to strain BLP005.

2. The method of claim 1, further comprising adding the isolated mutant strain to a food or feed product starting material.

* * * * *